(12) United States Patent
Evans et al.

(10) Patent No.: US 8,206,280 B2
(45) Date of Patent: Jun. 26, 2012

(54) ADJUSTABLE TISSUE SUPPORT MEMBER

(75) Inventors: Doug Evans, Snellville, GA (US);
Henry Holsten, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 803 days.

(21) Appl. No.: 12/269,749

(22) Filed: Nov. 12, 2008

(65) Prior Publication Data

US 2009/0137862 A1 May 28, 2009

Related U.S. Application Data

(60) Provisional application No. 60/987,469, filed on Nov. 13, 2007, provisional application No. 61/015,741, filed on Dec. 21, 2007, provisional application No. 61/020,231, filed on Jan. 10, 2008, provisional application No. 61/025,461, filed on Feb. 1, 2008, provisional application No. 61/102,147, filed on Oct. 2, 2008.

(51) Int. Cl.
*A61F 2/00* (2006.01)

(52) U.S. Cl. .............................. 600/37; 600/29; 606/151

(58) Field of Classification Search .............. 600/29–32, 600/37; 128/885, 897–899; 606/151, 157
See application file for complete search history.

(56) References Cited

U.S. PATENT DOCUMENTS

| | | | |
|---|---|---|---|
| 4,452,245 A | 6/1984 | Usher | |
| 4,524,771 A | 6/1985 | McGregor et al. | |
| 4,655,221 A | 4/1987 | Devereux | |
| 5,013,316 A | 5/1991 | Goble et al. | |
| 5,112,344 A | 5/1992 | Petros et al. | |
| 5,333,624 A | 8/1994 | Tovey | |
| 5,337,736 A | 8/1994 | Reddy | |
| 5,380,334 A | 1/1995 | Torrie et al. | |
| 5,500,000 A | 3/1996 | Feagin et al. | |
| 5,562,685 A | 10/1996 | Mollenauer et al. | |
| 5,562,689 A | 10/1996 | Green et al. | |
| 5,601,558 A | 2/1997 | Torrie et al. | |
| 5,643,320 A | 7/1997 | Lower et al. | |
| 5,662,683 A | 9/1997 | Kay | |
| 5,667,513 A | 9/1997 | Torrie et al. | |
| 5,702,397 A | 12/1997 | Goble et al. | |
| 5,792,142 A | 8/1998 | Galitzer | |

(Continued)

FOREIGN PATENT DOCUMENTS

WO 9959477 A1 11/1999

(Continued)

OTHER PUBLICATIONS

Dec. 29, 2008 International Search Report in international application PCT/US2008/083381.

(Continued)

*Primary Examiner* — Charles A Marmor, II
*Assistant Examiner* — Carrie R Dorna
(74) *Attorney, Agent, or Firm* — Rutan & Tucker, LLP

(57) ABSTRACT

The present disclosure relates to implants having two arms and a support portion configured to support a body tissue, such as a urethra. The implants are anchored in soft tissue with tissue anchors having a plurality of barbs. The tissue anchors contain an aperture through which a portion of arm is maintained. A locking member is disposed within at least one of the arms to facilitate fixation of the arm to at least one of the anchors.

20 Claims, 12 Drawing Sheets

U.S. PATENT DOCUMENTS

| | | | |
|---|---|---|---|
| 5,934,283 | A | 8/1999 | Willem et al. |
| 5,935,138 | A | 8/1999 | McJames, II et al. |
| 5,993,459 | A | 11/1999 | Larsen et al. |
| 6,056,688 | A | 5/2000 | Benderev et al. |
| 6,068,648 | A | 5/2000 | Cole et al. |
| 6,086,591 | A | 7/2000 | Bojarski |
| 6,096,041 | A | 8/2000 | Gellman et al. |
| 6,096,060 | A | 8/2000 | Fitts et al. |
| 6,110,101 | A | 8/2000 | Tihon et al. |
| 6,200,330 | B1 | 3/2001 | Benderev et al. |
| 6,273,852 | B1 | 8/2001 | Lehe et al. |
| 6,290,702 | B1 | 9/2001 | Fucci et al. |
| 6,293,961 | B2 | 9/2001 | Schwartz et al. |
| 6,306,159 | B1 | 10/2001 | Schwartz et al. |
| 6,319,271 | B1 | 11/2001 | Schwartz et al. |
| 6,322,492 | B1 | 11/2001 | Kovac |
| 6,328,686 | B1 | 12/2001 | Kovac |
| 6,328,758 | B1 | 12/2001 | Tornier et al. |
| 6,346,109 | B1 | 2/2002 | Fucci et al. |
| 6,355,065 | B1 | 3/2002 | Gabbay |
| 6,406,423 | B1 | 6/2002 | Scetbon et al. |
| 6,432,123 | B2 | 8/2002 | Schwartz et al. |
| 6,478,727 | B2 | 11/2002 | Scetbon et al. |
| 6,491,714 | B1 | 12/2002 | Bennett |
| 6,506,190 | B1 | 1/2003 | Walshe |
| 6,537,198 | B1 | 3/2003 | Vidlund et al. |
| 6,544,267 | B1 | 4/2003 | Cole et al. |
| 6,569,188 | B2 | 5/2003 | Grafton et al. |
| 6,575,976 | B2 | 6/2003 | Grafton |
| 6,575,984 | B2 | 6/2003 | Beyar et al. |
| 6,575,998 | B2 | 6/2003 | Beyar et al. |
| 6,592,610 | B2 | 7/2003 | Beyar et al. |
| 6,638,211 | B2 | 10/2003 | Suslian et al. |
| 6,641,524 | B2 | 11/2003 | Kovac |
| 6,652,450 | B2 * | 11/2003 | Neisz et al. ............... 600/30 |
| 6,656,183 | B2 | 12/2003 | Colleran et al. |
| 6,673,010 | B2 | 1/2004 | Skiba et al. |
| 6,689,047 | B2 | 2/2004 | Gellman |
| 6,691,711 | B2 | 2/2004 | Raz et al. |
| 6,712,830 | B2 | 3/2004 | Esplin |
| 6,730,110 | B1 | 5/2004 | Harari et al. |
| 6,746,472 | B2 | 6/2004 | Frazier et al. |
| 6,761,722 | B2 | 7/2004 | Cole et al. |
| 6,808,486 | B1 | 10/2004 | O'Donnell |
| 6,881,184 | B2 | 4/2005 | Zappala |
| 6,908,425 | B2 | 6/2005 | Luscombe |
| 6,911,003 | B2 | 6/2005 | Anderson et al. |
| 6,936,052 | B2 | 8/2005 | Gellman et al. |
| 6,960,160 | B2 | 11/2005 | Browning et al. |
| 6,971,390 | B1 * | 12/2005 | Vasek et al. ............... 604/533 |
| 6,986,781 | B2 | 1/2006 | Smith |
| 6,987,995 | B2 | 1/2006 | Drysen |
| 7,014,607 | B2 | 3/2006 | Gellman |
| 7,025,756 | B2 | 4/2006 | Frazier et al. |
| 7,033,380 | B2 | 4/2006 | Schwartz et al. |
| 7,037,255 | B2 | 5/2006 | Inman et al. |
| 7,037,324 | B2 | 5/2006 | Martinek |
| 7,044,905 | B2 | 5/2006 | Vidlund et al. |
| 7,056,333 | B2 | 6/2006 | Walshe |
| 7,070,556 | B2 | 7/2006 | Anderson et al. |
| 7,083,568 | B2 | 8/2006 | Neisz et al. |
| 7,083,648 | B2 | 8/2006 | Yu et al. |
| 7,094,199 | B2 | 8/2006 | Petros et al. |
| 7,204,801 | B2 | 4/2007 | Grocela |
| 7,204,802 | B2 | 4/2007 | De Leval et al. |
| D543,626 | S | 5/2007 | Watschke et al. |
| 7,226,407 | B2 | 6/2007 | Kammerer et al. |
| 7,226,408 | B2 | 6/2007 | Harai et al. |
| 7,235,043 | B2 | 6/2007 | Gellman et al. |
| 7,285,086 | B2 | 10/2007 | Smith et al. |
| 7,297,102 | B2 | 11/2007 | Smith et al. |
| 7,326,213 | B2 | 2/2008 | Benderev et al. |
| 7,347,812 | B2 | 3/2008 | Mellier et al. |
| 7,351,196 | B2 | 4/2008 | Goldmann et al. |
| 7,357,773 | B2 | 4/2008 | Watschke |
| 7,364,541 | B2 | 4/2008 | Chu et al. |
| 7,387,634 | B2 | 6/2008 | Benderev |
| 7,410,460 | B2 | 8/2008 | Benderev |
| 7,621,864 | B2 | 11/2009 | Suslian et al. |
| 7,771,345 | B1 * | 8/2010 | O'Donnell ............... 600/29 |
| 7,789,821 | B2 | 9/2010 | Browning |
| 7,981,023 | B2 * | 7/2011 | Nowlin et al. ............... 600/30 |
| 8,007,430 | B2 | 8/2011 | Browning |
| 8,057,383 | B2 | 11/2011 | Weiser et al. |
| 2001/0051807 | A1 | 12/2001 | Grafton |
| 2002/0091391 | A1 | 7/2002 | Cole et al. |
| 2002/0095181 | A1 | 7/2002 | Beyar |
| 2002/0165566 | A1 | 11/2002 | Ulmsten |
| 2002/0188301 | A1 | 12/2002 | Dallara et al. |
| 2003/0036770 | A1 | 2/2003 | Markman |
| 2003/0078604 | A1 | 4/2003 | Walshe |
| 2003/0088250 | A1 | 5/2003 | Colleran et al. |
| 2003/0135239 | A1 | 7/2003 | Gabriel et al. |
| 2003/0176875 | A1 | 9/2003 | Anderson et al. |
| 2003/0191360 | A1 | 10/2003 | Browning |
| 2003/0225424 | A1 | 12/2003 | Benderev |
| 2003/0229350 | A1 | 12/2003 | Kay |
| 2004/0039453 | A1 | 2/2004 | Anderson et al. |
| 2004/0044364 | A1 | 3/2004 | DeVries et al. |
| 2004/0059336 | A1 | 3/2004 | Lombardo et al. |
| 2004/0073219 | A1 | 4/2004 | Skiba et al. |
| 2004/0106847 | A1 | 6/2004 | Benderev |
| 2004/0106925 | A1 | 6/2004 | Culbert |
| 2004/0122474 | A1 | 6/2004 | Gellman et al. |
| 2004/0153008 | A1 | 8/2004 | Sharf et al. |
| 2004/0153074 | A1 | 8/2004 | Bojarski et al. |
| 2004/0153103 | A1 | 8/2004 | Schwartz et al. |
| 2004/0209538 | A1 | 10/2004 | Klinge et al. |
| 2004/0220595 | A1 | 11/2004 | Frazier et al. |
| 2004/0225181 | A1 | 11/2004 | Chu et al. |
| 2004/0230206 | A1 | 11/2004 | Gellman et al. |
| 2004/0231678 | A1 | 11/2004 | Fierro |
| 2004/0249240 | A1 | 12/2004 | Goldmann et al. |
| 2004/0249396 | A1 | 12/2004 | Lund et al. |
| 2004/0254609 | A1 | 12/2004 | Esplin |
| 2005/0004576 | A1 | 1/2005 | Benderev |
| 2005/0021086 | A1 | 1/2005 | De Leval |
| 2005/0038370 | A1 | 2/2005 | Kuth et al. |
| 2005/0065395 | A1 | 3/2005 | Mellier |
| 2005/0075654 | A1 | 4/2005 | Kelleher |
| 2005/0075660 | A1 | 4/2005 | Chu et al. |
| 2005/0131274 | A1 | 6/2005 | Suslian et al. |
| 2005/0131429 | A1 | 6/2005 | Ho et al. |
| 2005/0143618 | A1 | 6/2005 | Anderson et al. |
| 2005/0149122 | A1 | 7/2005 | McDevitt et al. |
| 2005/0228413 | A1 | 10/2005 | Binmoeller et al. |
| 2005/0234291 | A1 | 10/2005 | Gingras |
| 2005/0240076 | A1 | 10/2005 | Neisz et al. |
| 2005/0251083 | A1 | 11/2005 | Carr-Brendel et al. |
| 2005/0251159 | A1 | 11/2005 | Ewers et al. |
| 2005/0251177 | A1 | 11/2005 | Saadat et al. |
| 2005/0251202 | A1 | 11/2005 | Ewers et al. |
| 2005/0251210 | A1 | 11/2005 | Westra et al. |
| 2005/0256530 | A1 | 11/2005 | Petros |
| 2005/0273138 | A1 | 12/2005 | To et al. |
| 2005/0277806 | A1 | 12/2005 | Cristalli |
| 2005/0277966 | A1 | 12/2005 | Ewers et al. |
| 2005/0277981 | A1 | 12/2005 | Maahs et al. |
| 2005/0283040 | A1 | 12/2005 | Greenhalgh |
| 2005/0288689 | A1 | 12/2005 | Kammerer et al. |
| 2006/0041185 | A1 | 2/2006 | Browning |
| 2006/0058578 | A1 | 3/2006 | Browning |
| 2006/0063968 | A1 | 3/2006 | Anderson et al. |
| 2006/0089525 | A1 * | 4/2006 | Mamo et al. ............... 600/37 |
| 2006/0100628 | A1 | 5/2006 | Martinek |
| 2006/0106277 | A1 | 5/2006 | Romero Maroto |
| 2006/0116719 | A1 | 6/2006 | Martinek |
| 2006/0149123 | A1 | 7/2006 | Vidlund et al. |
| 2006/0183966 | A1 | 8/2006 | Neisz et al. |
| 2006/0184234 | A1 | 8/2006 | Frazier et al. |
| 2006/0195007 | A1 | 8/2006 | Anderson et al. |
| 2006/0196137 | A1 | 9/2006 | Brenzel et al. |
| 2006/0201519 | A1 | 9/2006 | Frazier et al. |
| 2006/0205995 | A1 | 9/2006 | Browning |
| 2006/0205998 | A1 | 9/2006 | Li et al. |
| 2006/0207606 | A1 | 9/2006 | Roue et al. |
| 2006/0217762 | A1 | 9/2006 | Maahs et al. |

| | | |
|---|---|---|
| 2006/0229493 A1 | 10/2006 | Weiser et al. |
| 2006/0229596 A1 | 10/2006 | Weiser et al. |
| 2006/0235262 A1 | 10/2006 | Arnal et al. |
| 2006/0235447 A1 | 10/2006 | Walshe |
| 2006/0247490 A1 | 11/2006 | Merade et al. |
| 2006/0252980 A1 | 11/2006 | Arnal et al. |
| 2006/0260618 A1 | 11/2006 | Hodroff et al. |
| 2006/0264698 A1 | 11/2006 | Kondonis et al. |
| 2006/0287571 A1 | 12/2006 | Gozzi et al. |
| 2007/0015957 A1 | 1/2007 | Li |
| 2007/0021649 A1 | 1/2007 | Nowlin et al. |
| 2007/0021686 A1 | 1/2007 | Gellman et al. |
| 2007/0038017 A1 | 2/2007 | Chu |
| 2007/0043255 A1 | 2/2007 | O'Donnell |
| 2007/0049791 A1 | 3/2007 | Merade et al. |
| 2007/0055094 A1 | 3/2007 | Chen |
| 2007/0055095 A1 | 3/2007 | Chu et al. |
| 2007/0068538 A1 | 3/2007 | Anderson et al. |
| 2007/0078295 A1 | 4/2007 | Landgrebe |
| 2007/0088390 A1 | 4/2007 | Paz et al. |
| 2007/0142698 A1 | 6/2007 | Bourne et al. |
| 2007/0156012 A1 | 7/2007 | Tracey et al. |
| 2007/0225546 A1 | 9/2007 | Anderson et al. |
| 2007/0299299 A1 | 12/2007 | Rosenblatt |
| 2007/0299300 A1 | 12/2007 | Smith et al. |
| 2008/0004490 A1 | 1/2008 | Bosley et al. |
| 2008/0009665 A1 | 1/2008 | Merade et al. |
| 2008/0009888 A1 | 1/2008 | Ewers et al. |
| 2008/0045782 A1 | 2/2008 | Jimenez |
| 2008/0097329 A1 | 4/2008 | Hodroff et al. |
| 2009/0221868 A1 | 9/2009 | Evans |
| 2010/0056856 A1 | 3/2010 | Suslian et al. |
| 2010/0197999 A1 | 8/2010 | Deegan et al. |

FOREIGN PATENT DOCUMENTS

| | | |
|---|---|---|
| WO | 2007097994 A2 | 8/2007 |

OTHER PUBLICATIONS

Dec. 29, 2008 Written Opinion of the International Searching Authority in international application PCT/US2008/083381.

* cited by examiner

ADJUSTABLE TISSUE SUPPORT MEMBER

The present application claims benefit of priority to U.S. Provisional Application Nos. 60/987,469, filed Nov. 13, 2007, titled "Implant with Adjustability Feature"; 61/015,741, filed Dec. 21, 2007, titled "Tissue Anchor Insertion Device"; 61/020,231 filed Jan. 10, 2008, titled "Continuous Knit Tubular Mesh Implant"; 61/025,461 filed Feb. 1, 2008, titled "Adjustable Tissue Support Member"; and 61/102,147, filed Oct. 2, 2008, titled "Adjustable Tissue Support Member," the disclosures of which are all incorporated herein by reference in their entirety.

Female urinary incontinence is commonly treated by a sling suspension procedure. Generally, sling suspension procedures involve the placement of a sling member beneath a patient's urethra. The sling member is suitably implanted in the patient's tissue with an introducer needle, which helps draw the sling into position.

Slings have been made of numerous materials, synthetic and natural, and are generally in the form of a mesh. A traditional sling procedure involves placing a strip of implant material (natural tissue, synthetic mesh, or a combination of the two) under the urethra and securing it to the rectus fascia or other portions of the patient's anatomy with sutures to hold the implant in position during the healing process.

Improved techniques have been developed that speed the implant process by reducing the number of incisions made and by altering the pathways by which the implant is introduced into the body. These improvements, which employ specialized instrumentation, help to reduce operative time and have made the procedure less invasive. The improved techniques generally require that an implant be joined to an introducer needle. The implant is then inserted into, and pulled through, the body. Subsequently, the implant is detached from the introducer needle.

Such procedures may require long needle passes and substantial tissue dissection, such as in the case of a retropubic or suprapubic procedure. Long needle passes increase the likelihood of an unintended perforation of a body structure (e.g., the bladder). In addition, the procedures typically require not only at least one vaginal incision, but also two external incisions at the locus of the obturator foramina in the case of a transobturator approach, and above the pubic bone in the retro- and suprapubic approaches.

Such procedures often use instrumentation that lacks an adjustability feature. A mesh sling has to exert an appropriate amount of tension on the urethra. Excessive tension can result in kinking of the urethra and/or undue tissue erosion, whereas insufficient tension can result in an ineffective sling. It might be desirable to be able to adjust the tension of the sling after both ends of the sling have been anchored in tissue, but before the tension is fixed and surgery is concluded. In addition, it could be desirable to provide bi-directional adjustment and not just adjustment in a single direction. Features that further the achievement of at least one of the foregoing goals could be desirable.

In view of the above, it would be beneficial to have a minimally invasive sling suitable for treating various conditions, such as incontinence, for example fecal and urinary incontinence, such as female urinary incontinence. According to various embodiments, each end of the implanted minimally invasive sling terminates in a tissue anchor. The length of the sling (and the tension exerted by the sling on the urethra) is configured for adjustment once at least one of the tissue anchors has been implanted.

SUMMARY

According to one embodiment, there is disclosed herein a tissue support system comprising an implantable tissue support member, wherein the implantable tissue support member comprises a tissue support portion having a length and a width, a first arm disposed at one end of the tissue support portion, and a second arm disposed at an opposite end of the tissue support portion, a first tissue anchor connected to the first arm, and a second tissue anchor connected to the second arm, wherein the second tissue anchor is slideable along a length of said second arm.

According to another embodiment, there is disclosed herein a tissue support system comprising an implantable tissue support member, wherein the implantable tissue support member comprises a tissue support portion having a first end and a second end, a first arm having a first end and a second end, wherein the first end is joined to the first end of the tissue support portion, a second arm having a first end and a second end, wherein the first end is joined to the second end of the tissue support portion, a first tissue anchor fixed to the second end of the first arm, and a second tissue anchor having an aperture therein, wherein the aperture is configured to at least partially enclose a portion of the second arm.

According to yet another embodiment, there is disclosed herein a method for providing support to body tissue, comprising making an incision in the vaginal wall, inserting an introducer needle having a first tissue anchor at the distal end thereof into the incision in the direction of the obturator membrane, wherein the first introducer needle is connected to an implant, ejecting the first tissue anchor from the introducer needle, withdrawing the introducer needle from the incision, and inserting a second tissue anchor in the distal end thereof wherein the second tissue anchor is connected to an implant, re-inserting the introducer needle into the incision in the direction of the contra-lateral obturator membrane, ejecting the second tissue anchor from the introducer needle, and applying traction to the implant until the desired amount of tissue support is obtained.

According to another embodiment, there is disclosed herein a medical device configured for implantation in tissue, comprising a lumen formed from a flexible material, at least one tissue anchor having at least one aperture therein, said at least one aperture configured to receive said lumen formed from a flexible material, and an anchor stop disposed in said lumen, wherein said anchor stop is configured to resist movement when urged in one direction within said lumen.

BRIEF DESCRIPTION OF THE DRAWINGS

The disclosed embodiments can be better understood with reference to the following drawings. The components in the drawings are not necessarily to scale.

DESCRIPTION

The following description should be read with reference to the drawings. The drawings, which are not necessarily to scale, depict selected embodiments and are not intended to limit the scope of the invention.

Figure 1:
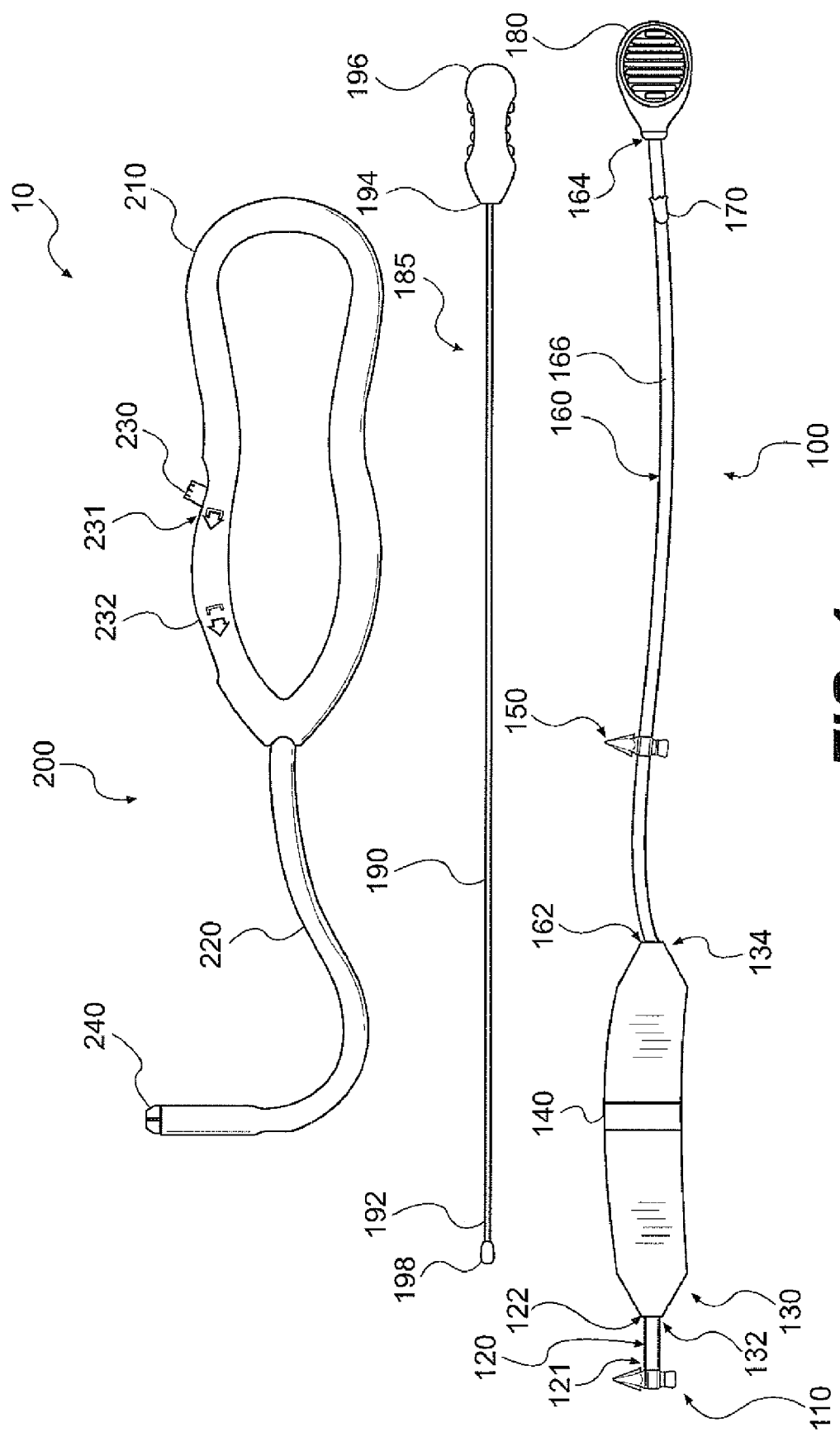
FIG. 1 illustrates one aspect of a tissue support system in accordance with the present disclosure.

FIG. 1 illustrates a tissue support system 10 according to various aspects of the present disclosure. The system includes an implantable tissue support member 100, a stylet 185, and an introducer needle 200. The tissue support member comprises a tissue support portion 130 having ends 132 and 134 connected to arms 120 and 160, and orienting indicia 140. The arm 129 has ends 121 and 122, and arm 160 has ends 162 and 164.

The orienting indicator 140 can comprise, by way of non-limiting example, a dyed centerline, or a colored thread woven into the center portion of the implant. According to one embodiment, the indicator is colored midline indicator in the form of a blue polypropylene thread woven through the middle of tissue support portion 130.

The implantable support member 100 further comprises a first tissue anchor 110, and a second tissue anchor 150. Tissue anchor 150 is configured to be connected to, but moveable along (i.e., slidably attached to), a length of arm 160. According to one embodiment, tissue anchor 150 slides along a length of arm 160. According to various embodiments, tissue anchor 150 has an aperture therein, through which arm 160 is received. According to certain embodiments, anchor 110 is fixed to end 121 of arm 120. According to another embodiment, anchor 110 is configured to be connected to, but moveable along, a length of arm 120.

According to one embodiment, tissue support portion 130 is a flat, single layer of mesh, and arms 120 and 160 are tubular mesh constructs. The tubular knit pattern allows for bi-directional adjustability of the implant once the tissue anchors 110 and 150 are in place. The arms are joined to the support feature via any suitable means, including by stitching, adhesive, sonic welding, and heat-staking. According to one embodiment, each of the arms is sewn to the tissue support portion 130 using the same type and size of polypropylene fiber from which the tissue support portion 130 and arms 120 and 160 are constructed.

According to another embodiment, tissue support portion 130 and arms 120 and 160 are constructed from a unitary tubular member having a single lumen running longitudinally therethrough. In such an embodiment, the diameter of the arms transition at 162 and 122 to form the tissue support portion 130. According to this embodiment, there is no joint at 162 or 122. According to various embodiments, the tubular mesh is smooth, providing a slight "ratcheting" effect during adjustment to give tactile feedback to the user.

Tubular mesh implants can be prepared by a number of known methods. For example, the tubular mesh can be manufactured by circular knitting, either single-ended or double-ended for added strength to provide a stable knit, uniform cross section, and smooth profile. The mesh can be manufactured by weft knitting via a "glove" style knitting machine to make smooth chain link stitches, which can allow diameter variation over a given length. According to another embodiment, the tubular mesh is a double warp knit, providing a high strength, multi-end knit using two flat mesh warp knits that are joined on the sides to make a tube mesh. According to another embodiment, the tubular mesh is made from a flat knitting machine, such as a Shimatronic® flat knitting machine sold by Shima Seiki Mfg., Ltd. of Wakayama, JP.

The mesh portions of implant 100 can have a single-strand or double-strand construction. According to certain embodiments, the tissue support portion 130 is a flat mesh comprising a knitted, open porosity, monofilament, polypropylene mesh strip. The open porosity of the mesh design and large pore sizes allow for macrophage penetration and the creation of an inert scaffold for tissue ingrowth to create a permanent support for the urethra. The pore sizes can be of any suitable diameter to allow tissue ingrowth. The tissue support portion 130 of implant 100 can have smaller pores ranging in diameter from 0.4 mm to 1.1 mm, for example 0.5 mm to 1.0 mm, such as 0.6 to 0.9 mm. The mesh can additionally have larger pores ranging in diameter from 0.8 mm to 1.3 mm, for example 1.0 mm to 1.2 mm.

According to one embodiment, the mesh is a polypropylene knit made from a small diameter fiber to create a soft and pliable material. According to various embodiments, the mesh is constructed so as to avoid, or at least minimize, curling of the implant upon application of a tensile force in the lengthwise direction. According to one embodiment, the mesh implant is a single-knit, double-stranded construction. The fibers can be of any suitable diameter. For example, the fibers can have a diameter ranging from 0.0015" to 0.100", for example 0.002", 0.0025", 0.003" or 0.004".

The implants disclosed herein can be constructed from different types of mesh. One suitable non-limiting example is a knitted polypropylene monofilament mesh fabric, such as BARD MESH from C. R. Bard, Inc. Other materials include SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). It is also contemplated that the mesh fabric may be formed from multifilament yarns and that any suitable method, such as knitting, weaving, braiding, molding, and the like, may be employed to form the prosthetic mesh material. The mesh may also be constructed from absorbable materials, such as polylactic acid. According to various embodiments, the mesh implants disclosed herein are manufactured via a knitting machine, such as a computerized Jacquard flat knitting machine.

The implants disclosed herein can include, or be constructed entirely from, a natural material. For example, the natural material can be disposed over at least one surface of the tissue support members disclosed herein. The natural material can be any suitable material including, but not limited to, biologically derived materials, such as cadaveric (human) or xenograft tissue (particularly of porcine or bovine origin)—for example dermis processed to make an acellular collagen scaffold or intestinal submucosa or other biological material and/or bioengineered materials. Collagen materials can be obtained from various sources, such as that available from Cook Biomedical, Inc. under the name COOK SURGISIS soft tissue graft. In one embodiment, the natural material comprises a cross-linked porcine dermal collagen material, such as COLLAMEND surgical implant from Davol (R. I.). Other suitable bioengineered materials may be employed as the present disclosure is not limited in this respect.

The arms 120 and 160 can have any width sufficient for the implant's intended purpose. For example, the arms can have a width ranging from 0.5 to 5.0 mm, including 1 mm to 5 mm, for example 2.0 mm to 4 mm, or 2.5 mm to 3.5 mm. The arms can have a length ranging from 10 mm to 100 mm, for example 20 mm to 60 mm, including 30 mm to 50 mm. According to various embodiments, tissue support portion 130 has a length ranging from about 30 mm to about 100 mm, for example about 40 mm to about 80 mm, including 65 mm. The support portion 130 can have any width sufficient to provide support to a body tissue. According to various embodiments, the width can range from 5 mm to 20 mm, for example 7 mm to 15 mm, including 10 mm to 14 mm. According to one embodiment, the width of tissue support portion 130 ranges from 5 mm to 15 mm, for example 10 mm to 12 mm. According to various embodiments, arms 120 and 160 have the same length, or substantially the same length. According to another embodiment, arms 120 and 160 have different lengths. For example, arm 120 is 5 mm to 20 mm long, for example 80 mm to 15 mm long, and arm 160 is 80 mm to 200 mm, for example 100 mm to 150 mm in length.

According to various embodiments, a tissue anchor can be fixed, either directly or indirectly (i.e., via a connector) to one or both of arms 120 and 160. Any anchor suitable for anchoring an implant to tissue, such as soft tissue, for example muscle tissue, a ligament, a tendon, or a membrane, such as the transobturator membrane, will suffice. The anchor may be fixed to the arms via any suitable means, including mechanically, by adhesive, friction fit, ultrasonic welding, solvent bonding, and heat staking.

According to various embodiments, a first tissue anchor 110 is configured to move freely along a length of arm 120, and a second anchor 150 is also configured to move freely along a length of arm 160. Once the anchors are implanted and the desired tension is obtained, both anchors can be fixed in position to arms 120 and 160. According to another embodiment, a first tissue anchor 110 is permanently fixed to the terminal end 121 of arm 120, and a second anchor 150 is configured to move freely along a length of arm 160. This facilitates the adjustment feature of the implant, such that once the first anchor and then the second anchor are implanted, the tension exerted on the urethra by the sling is adjusted by manipulating arm 160 in either direction relative to the anchor 150. The manipulation is via gripping feature 180, disposed at end 164 of arm 160. Once the desired tension is reached, the arm 160 is fixed in position to the anchor.

Figure 9B:
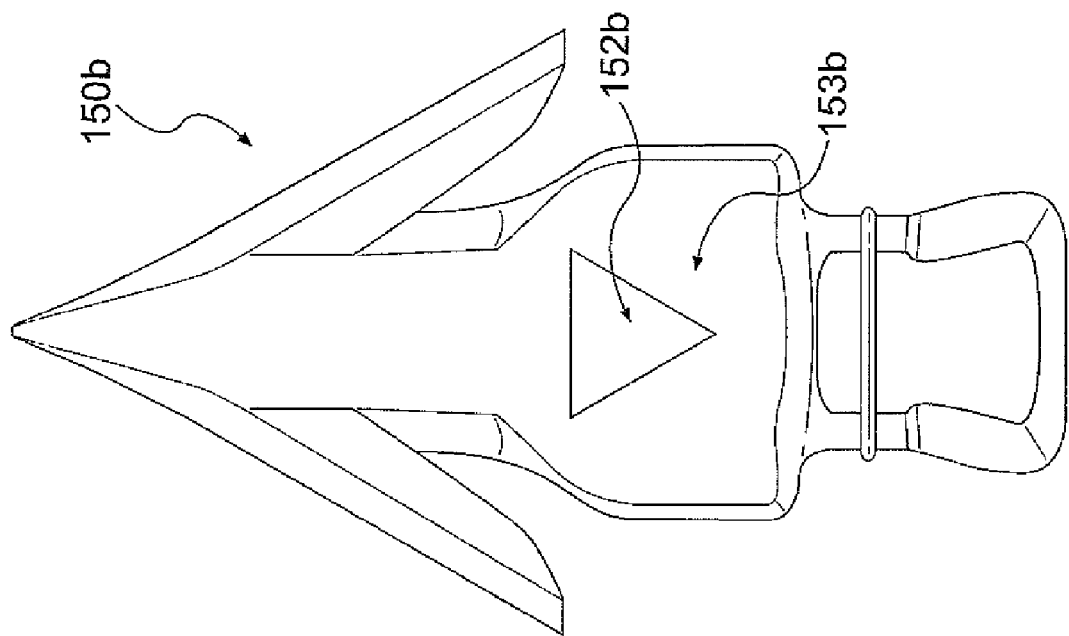
FIGS. 9A-9B illustrate cut-away views of exemplary tissue anchors.
Figure 9A:
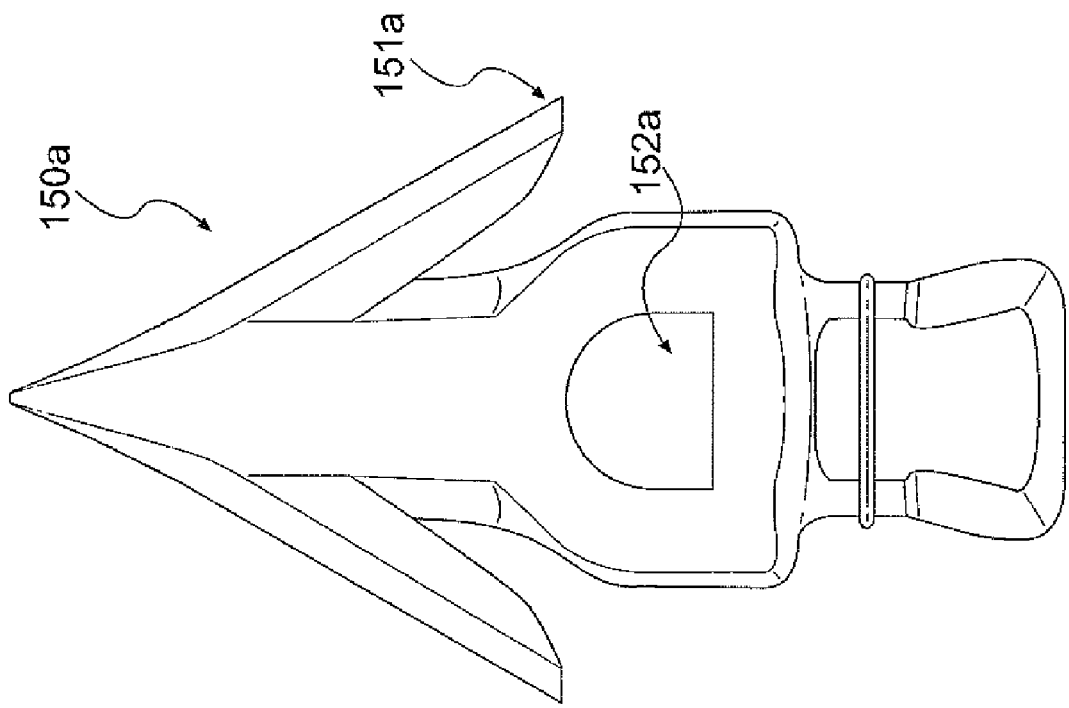
Figure 11:
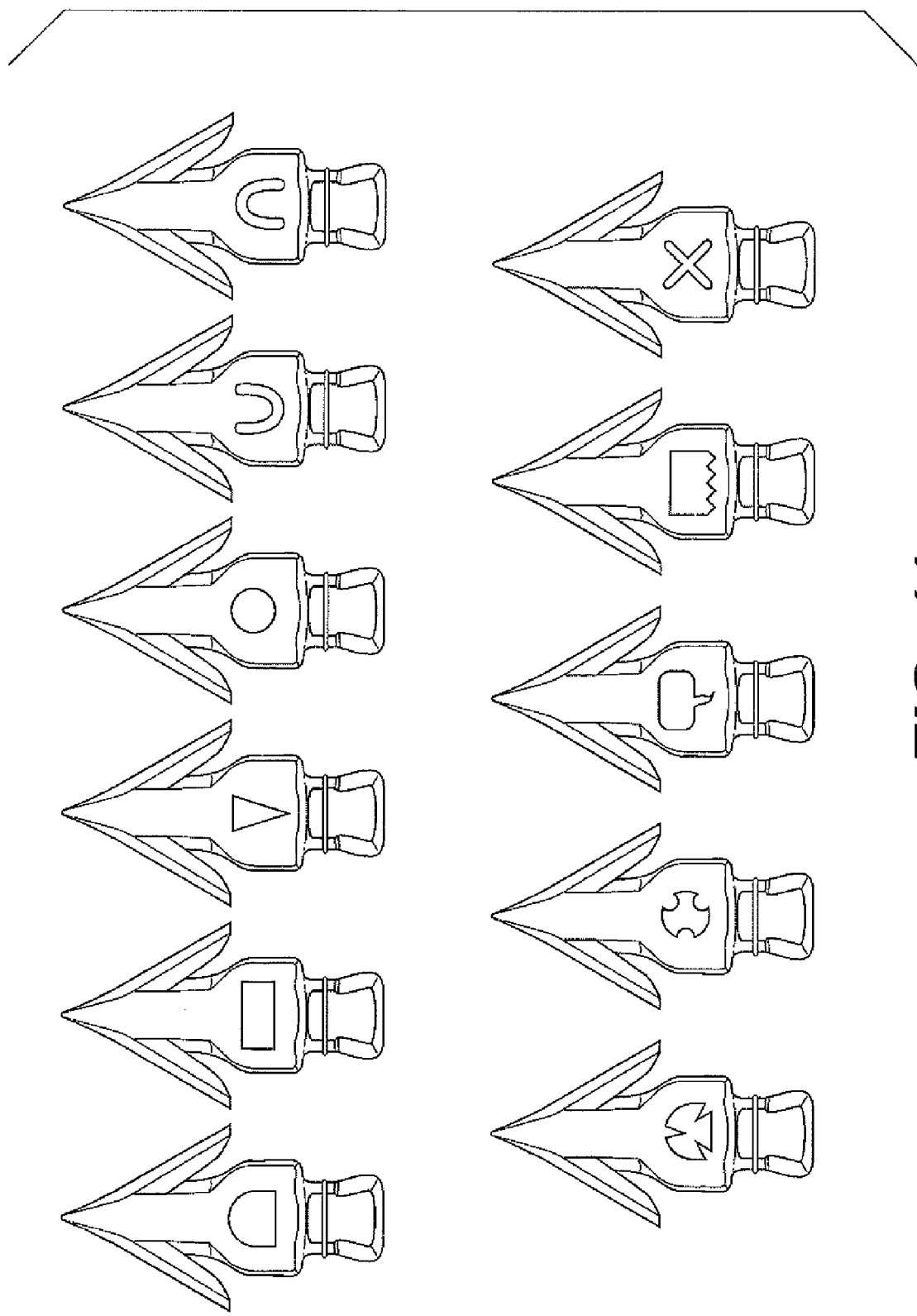
FIG. 11 illustrates cut-away views of exemplary tissue anchors.

According to one embodiment, at least one of the tissue anchors, such as tissue anchor 150, contains an aperture that is normal to the longitudinal axis of the anchor. This is illustrated in FIGS. 9A-9B and FIG. 11. FIG. 9A illustrates anchor 150a having barbs 151a, and aperture 152a configured to receive mesh arm 160. The aperture 151a and mesh arm 160 are respectively sized so that movement of arm 160 therethrough is restricted. The degree of restriction will depend on the fit between the arm and the edges of the aperture. According to one embodiment, the arm 160 and aperture 152a are relatively sized so that a slippage resistance in an amount of force ranging from 4 ounces to 6 pounds, for example 2 to 6 pounds, or 1 to 2 pounds, is required to pull 1 cm of the arm through the anchor aperture. FIG. 9B illustrates tissue anchor 150b having a triangularly-shaped aperture 152b. Arm 160 is received in aperture 152b, and exemplary feature 153b (the distal end of aperture 152b) assists in resisting movement of the arm. Additional exemplary tissue anchors are illustrated in FIG. 11.

Figure 12B:
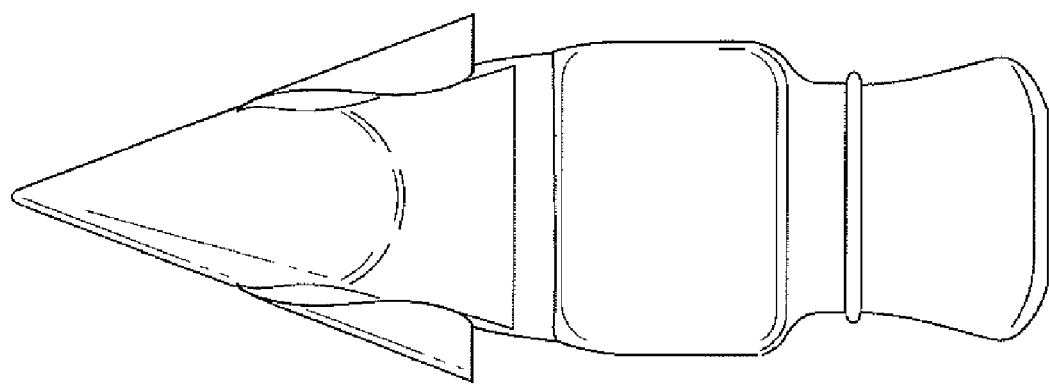
FIGS. 12A-12B illustrate bottom and side views of an exemplary tissue anchor.
Figure 12A:
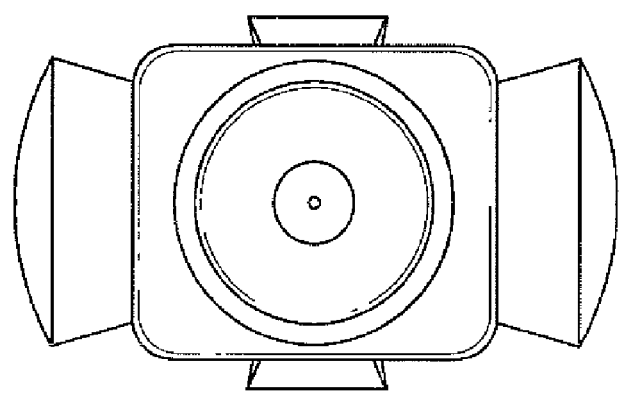

FIG. 12A illustrates a bottom view of an exemplary tissue anchor 150 according to the present disclosure. According to one embodiment, the tissue anchor has a longitudinal axis defined by a lumen. According to one embodiment, the lumen is configured to receive a pin that can pierce, and thereby anchor into position, arm 160. FIG. 12B illustrates a side view of tissue anchor 150.

Figure 10:
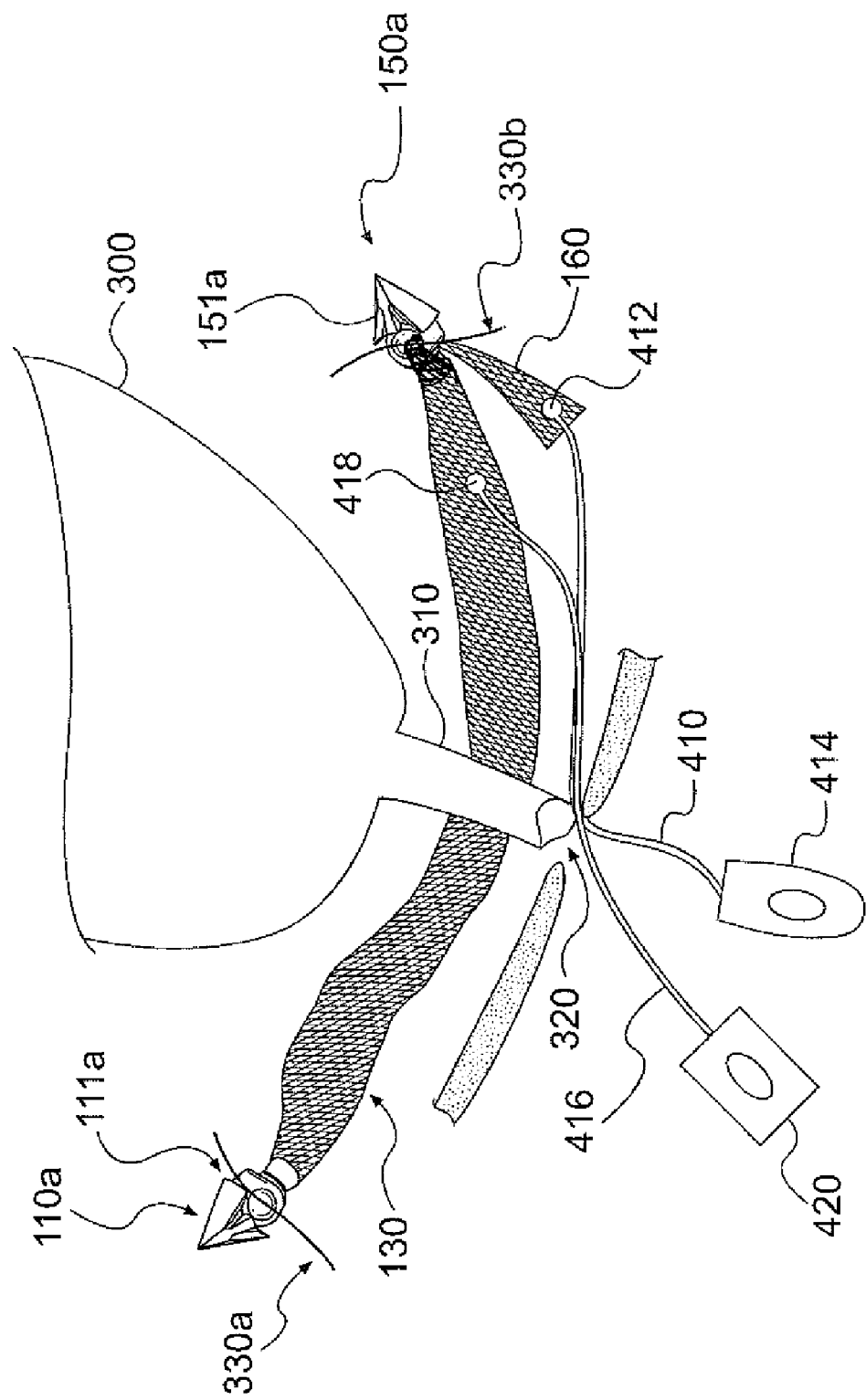
FIG. 10 illustrates an embodiment of a tissue support system.

FIG. 10 illustrates another embodiment in accordance with the present disclosure. A tissue support portion 130 is disposed underneath urethra 310 to assist in managing the flow of urine from bladder 300. Anchors 110a and 150a having barbs 111a and 151a, respectively, are anchored in the two obturator membranes 330a and 330b, respectively. A first adjustment suture 410 is attached to arm 160 at location 412. The distal end of first adjustment suture 410 is attached to tab 414. A second adjustment suture 416 is attached to tissue support portion 130 at location 418. The distal end of adjustment suture 416 is attached to tab 420. Both adjustment sutures 416 and 410 are configured to be disposed outside vaginal incision 320. According to various embodiments, and like the tissue anchors and the tissue support system, the adjustment sutures can be bioabsorbable.

Once the anchors 110a and 151a are securely anchored in the two obturator membranes, the surgeon may adjust the amount of tension exerted by tissue support portion 130 on urethra 310. According to one embodiment, the tension may be decreased by pulling suture 416 via tab 420. Alternatively, tension may be increased by pulling on suture 410 via tab 414. According to various embodiments, the adjustment sutures 410 and 416 may be differently colored to aid in identification. According to one embodiment, tabs 414 and 420 are differently shaped, differently colored, and/or marked to aid in distinguishing one suture from the other. According to another embodiment, sutures 410 and 416 are each in the form of a loop (not shown) that freely passes through respective points 412 and 418. That way, when the loops are cut following final tensioning of the implant, the entire length of suture is removed from the body.

According to various embodiments, immediately after the implant is tensioned, sutured 410 and 416 are cut and removed, and incision 320 is sutured closed. According to another embodiment, the implant is initially tensioned, and the incision is temporarily sutured and/or packed. The patient returns to the surgeon after 12 to 72 hours, and the patient's degree of continence or retention is reviewed. A final adjustment is made to the implant via tabs 414 and/or 420, the sutures 410 and 416 are cut and removed, and incision 320 is sutured closed.

The tissue anchors disclosed herein may be constructed from any biocompatible material, including stainless steel, polypropylene, and absorbable materials, including but not limited to polylactic acid, polyglactin, and polyglycolic acid, or other materials commonly used in absorbable surgical materials. According to various embodiments, the anchors disclosed herein can be of any dimension suitable to withstand particular pulling forces. The anchors can range in length from, for example, 5 mm to 20 mm, for example 10 mm to 15 mm, such as 10.1, 10.2, 10.3, 10.4, or 10.5 mm. The anchors have a thickness ranging from 1 mm to 5 mm, for example 2 mm to 3 mm thick. The anchors have a base of approximately 2.5 mm, for example 2.2 mm to 2.3 mm.

With reference to FIG. 1, the tissue support system 10 may further include stylet 185. Stylet 185 is configured for insertion into gripping feature 180, and then into the lumen 166 of arm 160. Stylet 185 includes a shaft 190 having a proximal end 194 and distal end 192, gripping feature 196, and a distal end 198. Stylet 185 can range in length from, for example, 12 cm to 25 cm, including 18 cm to 22 cm, such as 21 cm.

The tissue support system may further comprise introducer needle 200 having a handle 210, shaft 220, collet 240 configured to releasably secure a tissue anchor, and manually operable actuator 230. The actuator 230 is configured to secure a tissue anchor to the collet 240 when in position 231 (FIG. 2), and release the tissue anchor when moved to position 232

Figure 2:
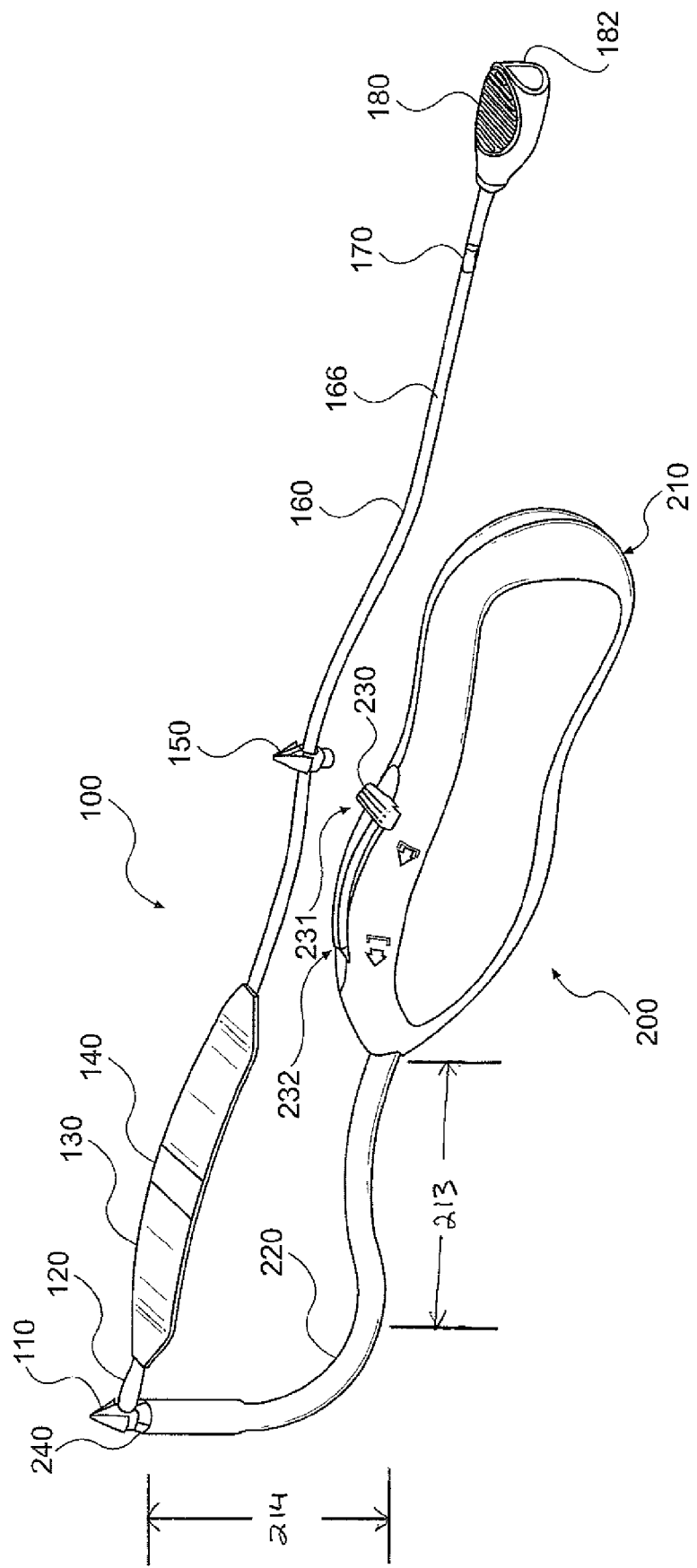
FIG. 2 illustrates an aspect of an implantable tissue support member and an introducer needle.
Figure 3:
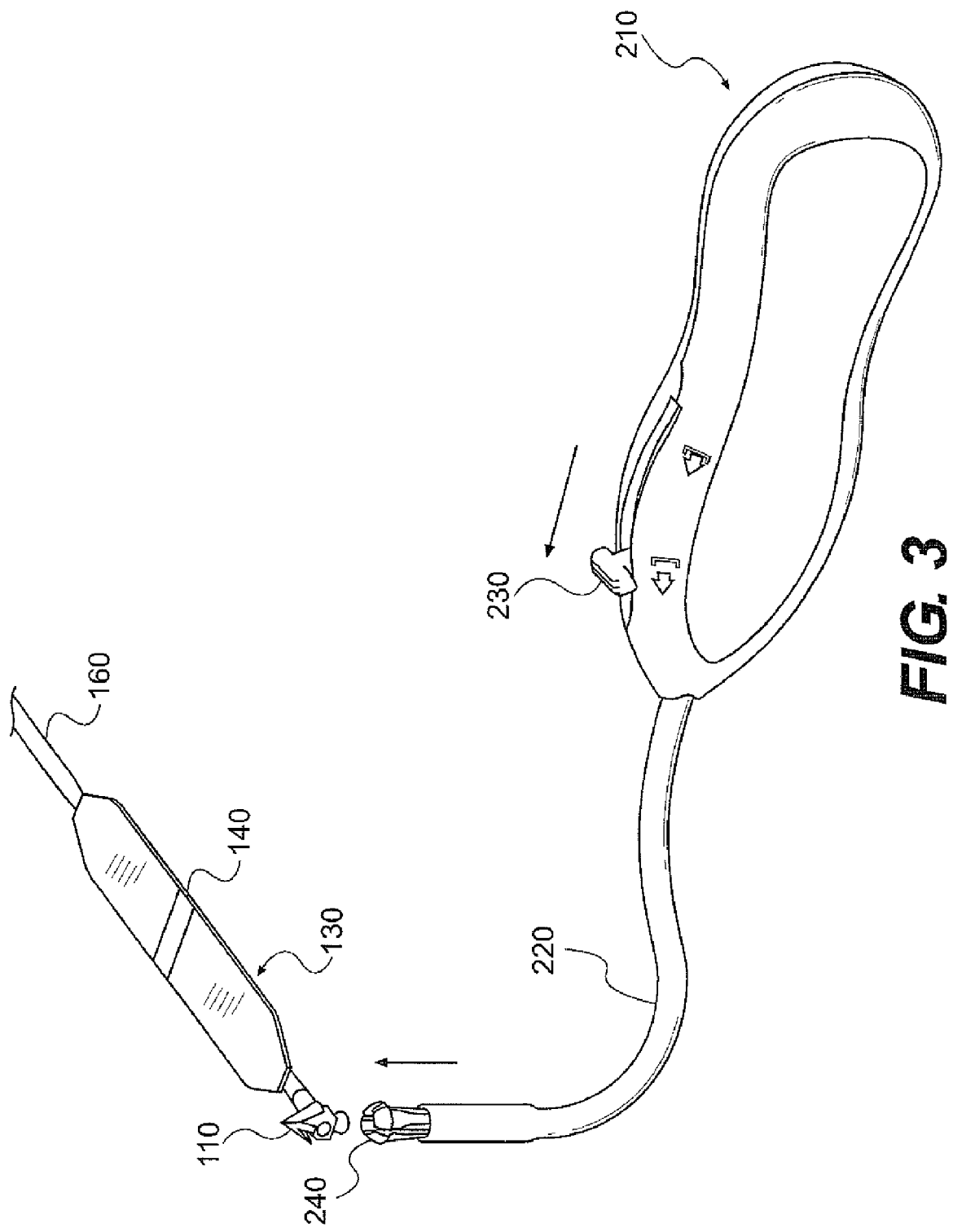
FIG. 3 illustrates a tissue anchor being released from an introducer needle.

(FIG. 3). The illustrated introducer needle 200 has a curved shaft 220, where the curve is in substantially the same plane as the handle. With reference to FIG. 2, shaft 220 can have a length 213 ranging from 3 cm to 7 cm, such as 4 cm to 6 cm, for example 5 cm. Shaft 220 can have a length 214 ranging from 3.5 cm to 5.5 cm, for example 4 cm to 5 cm, and 4.5 cm. According to various embodiments, shaft 220 is sized and shaped so that it snugly rotates around the ischiopubic ramus when an anchor is inserted in the region of the obturator foramen. According to another embodiment, the shaft has a helical shape. According to this embodiment, the system may be provided to a clinician with two helically-shaped needles, one for each side of a patient's anatomy.

FIGS. 1-6 illustrate locking member 170 disposed in lumen 166 in accordance with the present disclosure. According to various embodiments, the locking member 170 is constructed from polypropylene. The locking member 170 can have any size suitable for its intended purpose. By way of non-limiting example, the locking member has a diameter ranging from 1 mm to 2 mm, for example 1.2 mm to 1.8 mm, a width ranging from 1.5 mm to 2.5 mm, and a length ranging from 2.5 mm to 5.5 mm, for example 4.5 mm.

Figure 4:
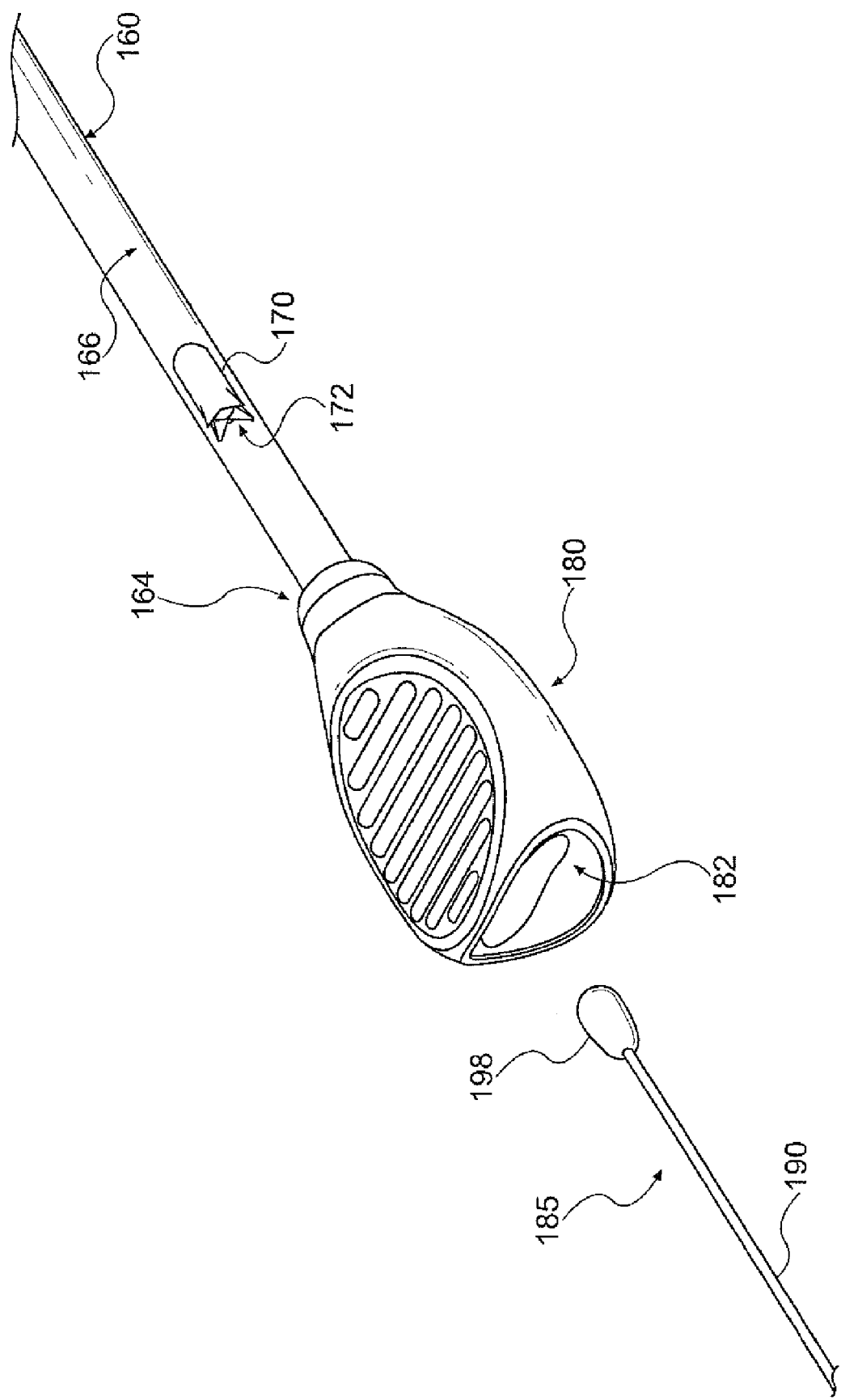
FIG. 4 illustrates a stylet being urged into a lumen.

With reference to FIG. 4, the locking member 170 is configured to be initially disposed within the lumen 166 of arm 160 at a location proximal to grasping feature 180. After anchor 150 is set in a desired tissue location, arm 160 is fixed in position relative to the locking feature until it abuts anchor 150. The sliding can be accomplished by insertion of flexible stylet 185 through lumen 182 in grasping feature 185, which lumen is in fluid communication with lumen 166 in arm 160. The distal end 198 of stylet 185 contacts locking member 170, and urges the locking member in the direction of anchor 150. Movement of the locking member in the reverse direction, i.e., towards end 164 of arm 160, is arrested by the prongs 172. When the anchor stop is urged towards the end 164, the prongs 170 will tend to anchor into the mesh, thus arresting further movement.

Figure 5:
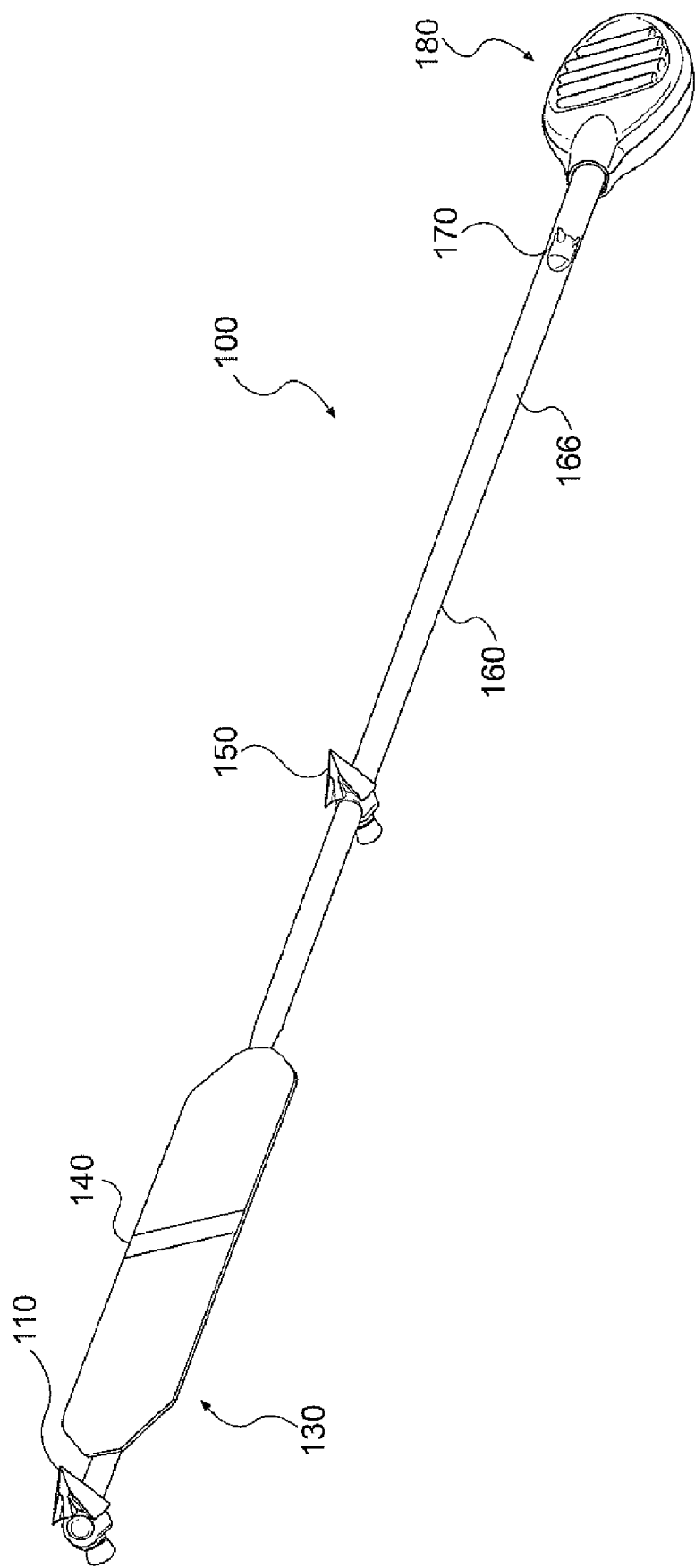
FIG. 5 illustrates a view of a tissue support member.
Figure 6:
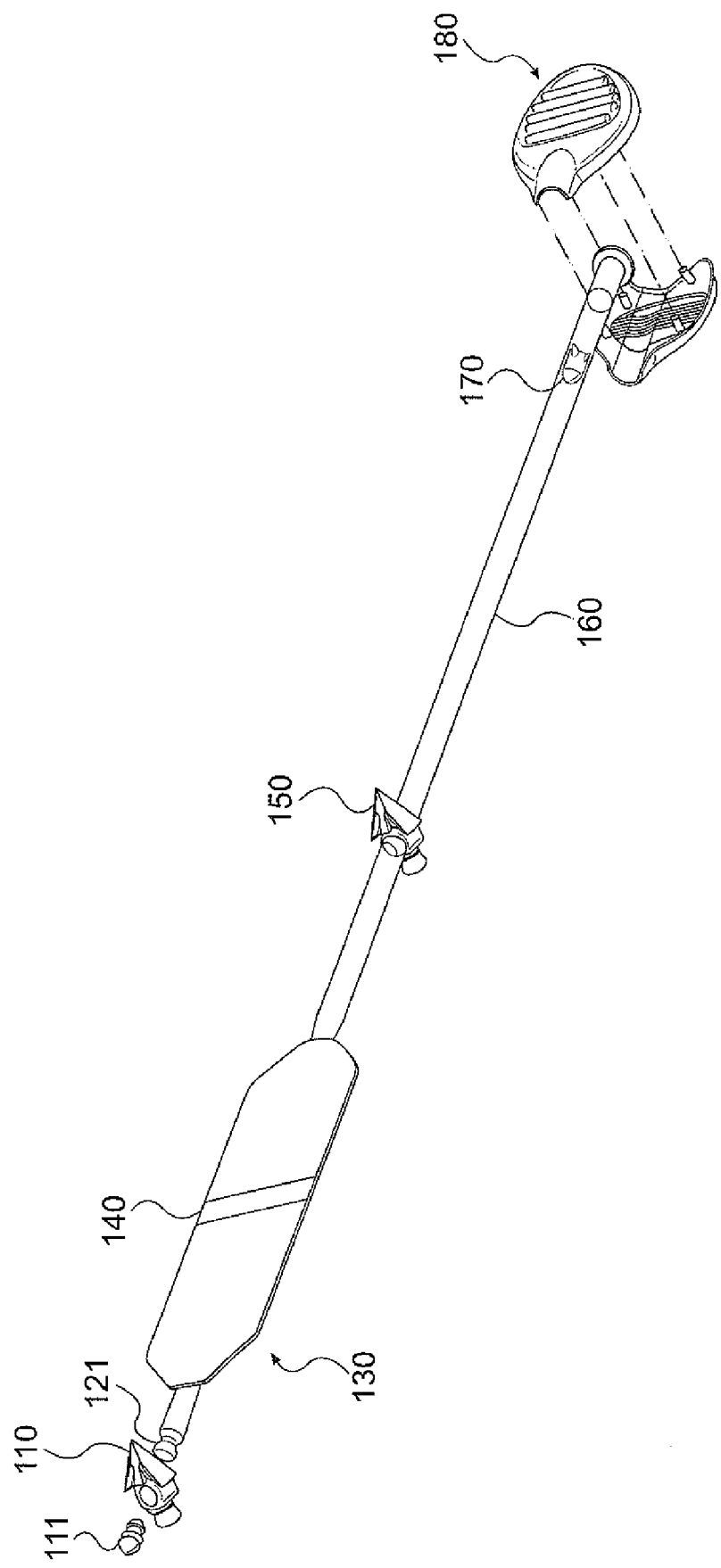
FIG. 6 illustrates an exploded view of a tissue support member.
Figure 7:
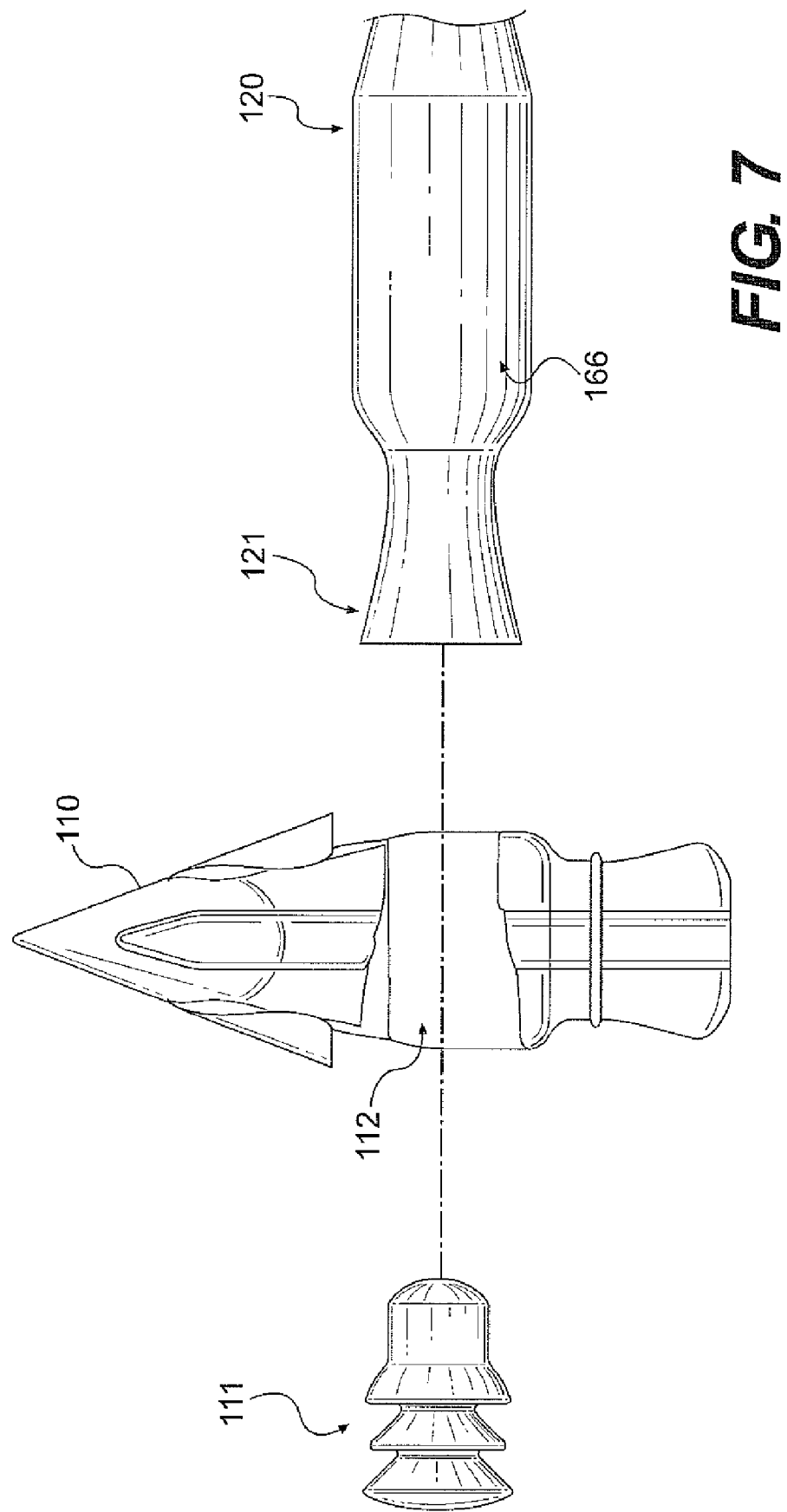
FIG. 7 illustrates a view of one aspect of a tissue support member.
Figure 8:
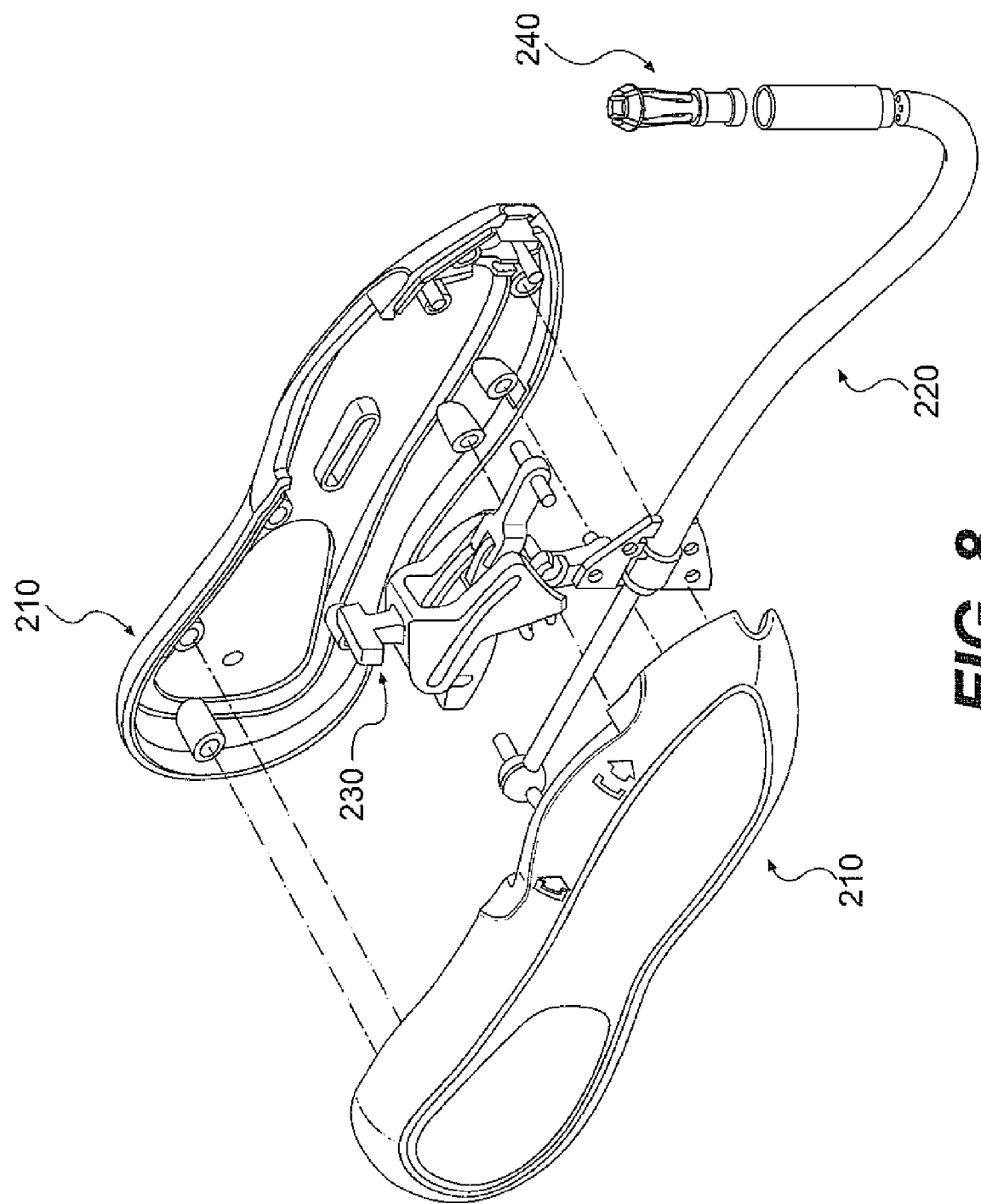
FIG. 8 illustrates an exploded view of an introducer needle.

FIG. 5 illustrates another view of the implantable tissue support member 100. FIG. 6 illustrates a partially exploded view of the tissue support member. FIG. 7 illustrates one embodiment of the fixation of anchor 110 to arm 120. End 121 of arm 120 is inserted into aperture 112 of anchor 110. Plug 111 is then inserted into lumen 166 and aperture 112, thereby providing a friction fit between the plug 112, the arm 120, and anchor 110.

The tissue support system in accordance with the present disclosure can be used to restore correct support to various types of tissue. For example, the system can be used to treat female and male urinary incontinence, for example stress incontinence. The system can be used to treat fecal incontinence. In addition, the system can be used for pelvic floor repair, such as pelvic organ prolapse, by fixing a tissue support portion to ligament and/or muscle for anterior, posterior, and apical vaginal vault repair.

According to one embodiment, the tissue support system disclosed herein comprises a urethral sling. According to one embodiment, a procedure for implanting the urethral sling generally comprises making a mid-urethral incision and dissecting the vaginal tissue out laterally in the direction of the superior-medial aspect of the obturator foramen. The ends of the sling are then passed through the obturator internus muscle/obturator membrane using an introducer device. According to one embodiment, two exit incisions are made in the groin to allow for exteriorization of the introducer needle and sling ends. These exit incisions allow for adjustment of the sling tension under the urethra using the free arms of the mesh at the exit incisions. According to another embodiment of the present disclosure, the urethral sling does not require any exit incisions because mesh adjustment can be done at the vaginal incision.

The following illustrates one way in which a tissue support system in accordance with the present disclosure may be used to treat female urinary incontinence. The patient is placed in a dorsal lithotomy position with hips in flexion at approximately 90 degrees and the buttocks even with the edge of the table. Standard operative preparation of the surgical site is completed, and the bladder is emptied with a Foley catheter. The mid-urethra is identified by first locating the external urethral meatus and then the bladder neck by identifying the Foley catheter bulb.

Hydro-dissection is performed by injecting a solution (e.g., 1% lidocaine with epinephrine) at the midline between the vaginal wall and urethra, thereby creating a urethro-vaginal space. Additional hydro-dissection can be performed by injecting solution laterally towards the cephalad aspect of the ischiopubic ramus in order to better identify the lateral sulci. Allis clamps are placed at the level of the mid-urethra on the anterior vaginal wall.

A small (approximately 1.5 cm) incision is made in the anterior vaginal wall beginning approximately 1 cm under the urethral meatus. The depth of the incision may extend into the vaginal muscularis. The urethra is gently freed from the anterior vaginal wall. Next, dissection is made using scissors (e.g., Metzenbaum scissors) laterally in a 45 degree angle until the tip of the scissors makes contact with the medial-cephalad aspect of the ischiopubic ramus (approximately 1-2 cm). This procedure is then repeated on the contralateral side.

The introducer needle 200 is loaded with anchor 110, as shown in FIG. 2. The introducer is then inserted into the vaginal dissection laterally through one of the dissected planes toward the cephalad aspect of the ischiopubic ramus. The introducer 200 is angled towards the superior-medial aspect of the obturator foramen. Once the fixed anchor is behind the ischiopubic ramus, anchor 110 is pushed into the tissue until it is slightly beyond the ramus.

The handle 210 is pivoted to insert the anchor 110 through the obturator internus muscle/membrane at the superior-medial aspect of the obturator foramen, such that the orienting indicia 140 is at or slightly past the midurethra (about 0.5 cm) in the direction of insertion. A distinctive pop may be heard, indicating perforation of the muscle/membrane. The anchor 110 is released by pushing the actuator 230 forward from position 231 to position 232 in the introducer handle 210. The introducer is then gently retracted by reversing through the insertion path.

After anchor 110 is released from collet 240, gentle traction is applied to the sub-urethral sling to confirm secure fixation in the tissue.

Next, adjustable anchor 150 is loaded into the introducer and secured by retracting the manual actuator 230 on the handle 210 from position 232 to position 231. A slight "click" may be felt or heard, confirming secure loading. At this point in the procedure, care is taken to ensure the implant is not twisted.

Next, it may be desirable to confirm at least 4 cm of adjustable mesh between the tissue support portion 130 and the anchor 150 prior to insertion.

The anchor 150 is inserted in the contralateral dissection plane, and the introducer needle 200 is oriented towards the superior-medial aspect of the obturator foramen. Anchor 150 is pushed into the tissue slightly beyond the ischiopubic ramus, and handle 210 is pivoted to insert anchor 150 through the obturator internus muscle/membrane in the superior-medial aspect of the obturator foramen.

Anchor 150 is released from collet 240 by pushing the actuator 230 from position 231 to position 232 in the introducer handle 210. Introducer needle 200 is retracted by reversing through the insertion path. After anchor 150 is released, gentle traction is applied on the tissue support system 100 to confirm secure fixation in the tissue.

Grasping feature 180 is gently pulled to adjust the tension exerted by the tissue support portion 130 on the urethra. To aid in adjustment, a finger is inserted vaginally to stabilize anchor 150 at the obturator internus muscle. The sling can also be loosened by using gentle counter-traction on the tissue support portion 130 on the side closest to anchor 150. A thin, blunt instrument (such as a hemostat) between the urethra and the sub-urethral sling may be used as a spacer to aid in setting the appropriate tension. A cough or créde test can also be employed to achieve the appropriate tension. The orienting indicia 140 should be visible at the midline, no more than 1 cm away from the urethra in either direction.

Once proper tensioning is achieved, stylet 185 is inserted into lumen 182 of gripping feature 180. The stylet 185 is inserted into lumen 166 to urge locking member 170 into place at anchor 150. When properly seated, the stylet 185 will bow, signifying that the locking member 170 is in the proper location and the tissue support member has been secured. Once anchor 150 is locked into position, additional tightening can be achieved using the gripping feature 180.

Stylet 185 is removed after final securement of the tissue support member 100. According to one embodiment, arm 160 is cut between anchor 150 and end 164. The vaginal incision is then closed using suture. According to various embodiments, the incision is temporarily closed and packed around arm 160. This would allow the clinician to post-operatively modify the amount tension exerted by the implant on the urethra. Once desired degree of tension is obtained and confirmed, the anchor 150 can optionally be fixed to arm 160, and the remaining material can be cut and, in the case wherein the implant is constructed of non-bioabsorbable material, be removed from the body.

According to various embodiments, a sheath can enclose at least a portion of the tissue support member disclosed herein to facilitate their passage into tissue. In such an embodiment, the tissue support member, or at least the support portion thereof, is sandwiched between two sheaths. The sheath sides are suitably made out of a material with a low coefficient of friction, such as polytetrafluoroethylene (PTFE). According to another embodiment, the tissue support member is implanted without a sheath.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Also, unless otherwise indicated, all numbers expressing quantities of physical parameters and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Numerical ranges given throughout this specification will include every narrower numerical range that falls within such broader numerical range, as if such narrower numerical ranges were all expressly written herein.

Claimed is:

1. A tissue support system including an implantable tissue support member, comprising:
    a tissue support portion;
    a first arm having a first end joined to a first end of the tissue support portion;
    a second arm constructed of mesh including a lumen formed by a tubular knit construction of the mesh, the second arm having a first end joined to a second end of the tissue support portion;
    a first tissue anchor fixed to a second end of the first arm;
    a second tissue anchor having an aperture therein, the aperture at least partially enclosing a portion of the second arm; and
    a locking member disposed in the lumen of the second arm between the second tissue anchor and a second end of the second arm.

2. The tissue support system according to claim 1, wherein the aperture is configured to resist unconstrained movement of the second arm therethrough.

3. The tissue support system according to claim 1, wherein the locking member is configured to be urged in the direction of the second anchor, and to resist movement in the direction of the second end of the second arm.

4. The tissue support system according to claim 1, further comprising a stylet configured for introduction into the lumen from the second end of the second arm, and for urging the locking member in the direction of the second anchor.

5. The tissue support system according to claim 1, further comprising an introducer needle configured to releasably secure a tissue anchor.

6. The tissue support system according to claim 5, wherein the introducer needle comprises a shaft and a handle.

7. The tissue support system according to claim 6, wherein the shaft has a curved portion.

8. The tissue support system according to claim 7, wherein the shaft has a substantially helical shape.

9. The tissue support system according to claim 6, wherein the introducer needle comprises a collet at the distal end of the shaft.

10. The tissue support system according to claim 6, wherein the handle comprises a manually operable mechanism for releasing the anchor from the distal end of the shaft.

11. The tissue support system according to claim 1, wherein the tissue support portion comprises orientating indicia.

12. The tissue support system according to claim 11, wherein the orientating indicia comprises a colored feature in the center of the tissue support portion.

13. A method for providing support to body tissue, comprising:
    making an incision in the vaginal wall;
    inserting an introducer needle having a first tissue anchor at the distal end thereof into the incision in the direction of the obturator membrane, wherein the first introducer needle is connected to an implant;
    ejecting the first tissue anchor from the introducer needle;
    withdrawing the introducer needle from the incision, and inserting a second tissue anchor in the distal end thereof, wherein the second tissue anchor is connected to the implant, the implant including a lumen that passes through an aperture in the second tissue anchor, and wherein a locking feature is disposed in the lumen for urging in a first direction, the locking feature resisting movement in a second direction opposite of the first direction;
    re-inserting the introducer needle into the incision in the direction of the contra-lateral obturator membrane;
    ejecting the second tissue anchor from the introducer needle; and
    applying traction to the implant until the desired amount of tissue support is obtained.

14. The method according to claim 13, further comprising locking the implant to the second tissue anchor by urging the locking feature through the lumen of the implant and into the aperture of the second tissue anchor.

15. The method according to claim 14, wherein the implant is locked to the second tissue anchor via a frictional fit of the locking feature in the aperture.

16. The method according to claim 14, wherein the step of locking the implant to the second tissue anchor is performed immediately after the applying traction step.

17. The method according to claim 14, wherein the step of locking the implant to the second tissue anchor is performed from 12-72 hours after the applying traction step.

18. The method according to claim 13, wherein the body tissue is the urethra.

19. The method according to claim 13, wherein the body tissue is the bladder.

20. A method for providing support to body tissue, comprising:
    making an incision in the vaginal wall;
    inserting an introducer needle having a first tissue anchor at the distal end thereof into the incision in the direction of the obturator membrane, wherein the first introducer needle is connected to an implant;
    ejecting the first tissue anchor from the introducer needle;
    withdrawing the introducer needle from the incision, and inserting a second tissue anchor in the distal end thereof, wherein the second tissue anchor is connected to the implant, the implant including a lumen that passes through an aperture in the second tissue anchor;
    re-inserting the introducer needle into the incision in the direction of the contra-lateral obturator membrane;
    ejecting the second tissue anchor from the introducer needle;
    applying traction to the implant until the desired amount of tissue support is obtained; and
    locking the implant to the second tissue anchor by urging an anchor stop disposed in the implant lumen toward the second tissue anchor and into the second tissue anchor aperture.

* * * * *